(12) United States Patent (10) Patent No.: US 12,696,968 B2

Keum et al. (45) Date of Patent: Aug. 4, 2026

(54) ULTRASONIC MASK AND SKIN CARE DEVICE COMPRISING SAME

(71) Applicant: LG INNOTEK CO., LTD., Seoul (KR)

(72) Inventors: Do Hee Keum, Seoul (KR); Min Seok Oh, Seoul (KR); Sang Young Lee, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 1078 days.

(21) Appl. No.: 17/437,083

(22) PCT Filed: Feb. 26, 2020

(86) PCT No.: PCT/KR2020/002713

§ 371 (c)(1),
(2) Date: Sep. 8, 2021

(87) PCT Pub. No.: WO2020/184868

PCT Pub. Date: Sep. 17, 2020

(65) Prior Publication Data

US 2022/0160111 A1 May 26, 2022

(30) Foreign Application Priority Data

Mar. 11, 2019 (KR) ........................ 10-2019-0027304

(51) Int. Cl.
*A45D 44/00* (2006.01)
*A61M 37/00* (2006.01)

(52) U.S. Cl.
CPC ...... *A45D 44/002* (2013.01); *A45D 2200/207* (2013.01); *A61M 37/0092* (2013.01); *A61M 2205/0294* (2013.01)

(58) Field of Classification Search
CPC ........... A45D 44/002; A45D 2200/207; A61M 37/0092; A61M 2205/0294; A61M 35/10;
(Continued)

(56) References Cited

U.S. PATENT DOCUMENTS

2008/0139943 A1* 6/2008 Deng ................ A61M 37/0092
600/459
2010/0241056 A1* 9/2010 Lehtoluoto ............ A61N 1/328
604/20
(Continued)

FOREIGN PATENT DOCUMENTS

CN 101195059 6/2008
CN 109395241 3/2019
(Continued)

OTHER PUBLICATIONS

International Search Report dated Jun. 10, 2020 issued in Application No. PCT/KR2020/002713.
(Continued)

*Primary Examiner* — Rebecca E Eisenberg
*Assistant Examiner* — Kate Elizabeth Strachan
(74) *Attorney, Agent, or Firm* — KED & ASSOCIATES, LLP

(57) ABSTRACT

An ultrasonic mask according to an embodiment comprises: a first substrate; a first wire disposed on the upper surface of the first substrate; a second substrate disposed above the first substrate; a second wire disposed on the lower surface of the second substrate; a piezoelectric member between the first substrate and the second substrate; a first electrode connected to the first wire and disposed on the lower surface of the piezoelectric member; and a second electrode connected to the second wire and disposed on the upper surface of the piezoelectric member, wherein the first wire and the second wire have curvatures (mm) of 5R to 15R, and the piezoelectric member generates an ultrasonic wave having a frequency band of 20 kHz to 1 MHz.

15 Claims, 9 Drawing Sheets

(58) Field of Classification Search
CPC ................ A61H 23/02; A61H 23/0245; A61H
2201/105; A61N 7/00; A61N 2007/0034
See application file for complete search history.

(56) References Cited

U.S. PATENT DOCUMENTS

| | | | | |
|---|---|---|---|---|
| 2011/0204993 | A1* | 8/2011 | Masuda | H01L 23/66 |
| | | | | 333/136 |
| 2013/0197550 | A1 | 8/2013 | Dietz et al. | |
| 2014/0076612 | A1* | 3/2014 | Kuriki | G06F 3/041 |
| | | | | 174/250 |
| 2015/0209564 | A1* | 7/2015 | Lewin | A61M 37/0092 |
| | | | | 601/2 |
| 2017/0189227 | A1* | 7/2017 | Brunson | A61N 1/325 |
| 2017/0215846 | A1* | 8/2017 | Sammoura | B06B 1/0666 |
| 2017/0347891 | A1* | 12/2017 | Rogers | A61B 5/4848 |
| 2019/0267995 | A1 | 8/2019 | Du et al. | |
| 2020/0114135 | A1* | 4/2020 | Paolini, Jr. | A61N 1/0428 |

FOREIGN PATENT DOCUMENTS

| | | |
|---|---|---|
| JP | 2002-153461 | 5/2002 |
| JP | 2005-118527 | 5/2005 |
| JP | 2006-158171 | 6/2006 |
| JP | 2015-084942 | 5/2015 |
| KR | 20-2000-0017512 | 9/2000 |
| KR | 10-2012-0113105 | 10/2012 |
| KR | 10-2016-0035202 | 3/2016 |
| KR | 10-2016-0035204 | 3/2016 |
| KR | 20160035204 A * | 3/2016 |
| KR | 20-0481053 | 8/2016 |
| WO | WO 2018/090892 | 5/2018 |

OTHER PUBLICATIONS

Chinese Office Action dated Sep. 9, 2022 issued in Application No. 202080020849.9.

* cited by examiner

【FIG. 1】
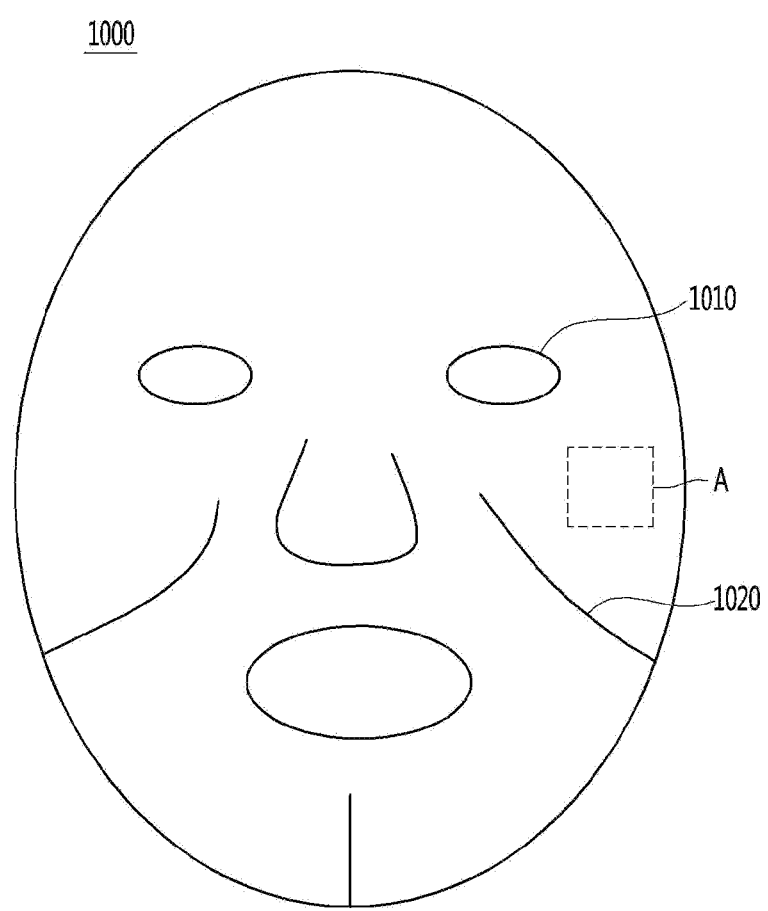

【FIG. 2】
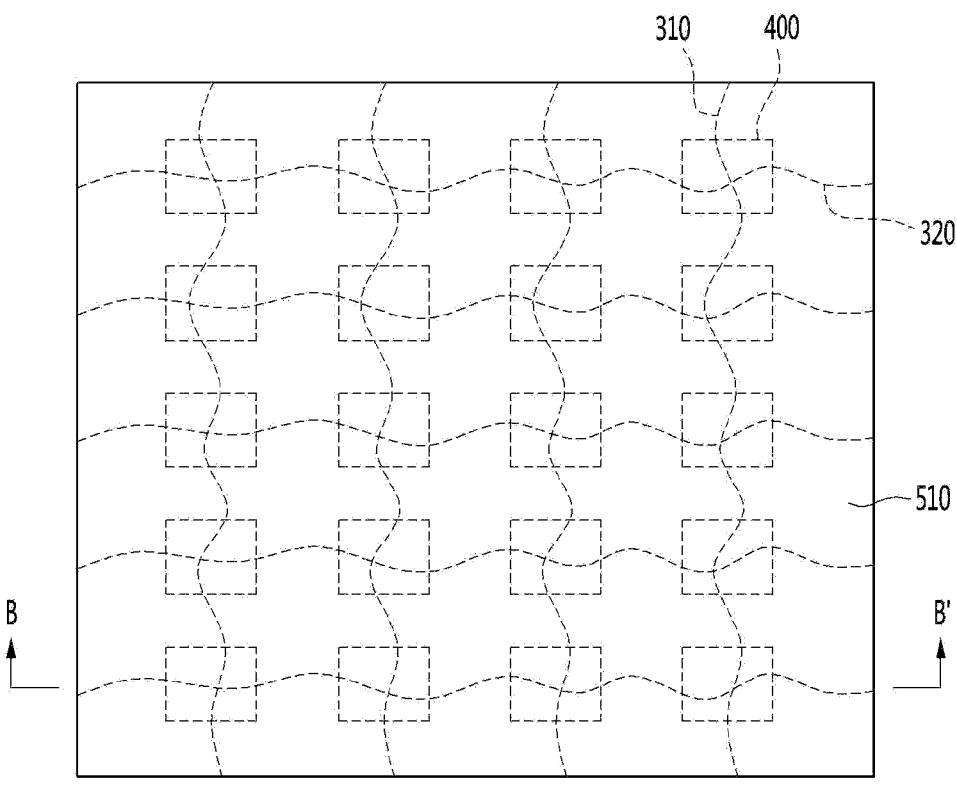
【FIG. 3】
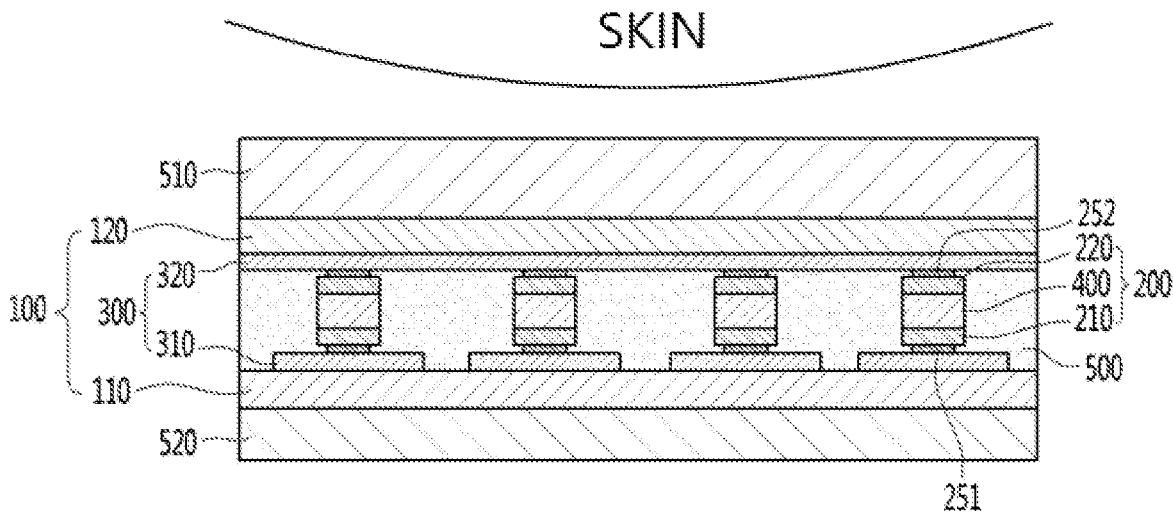

【FIG. 4】
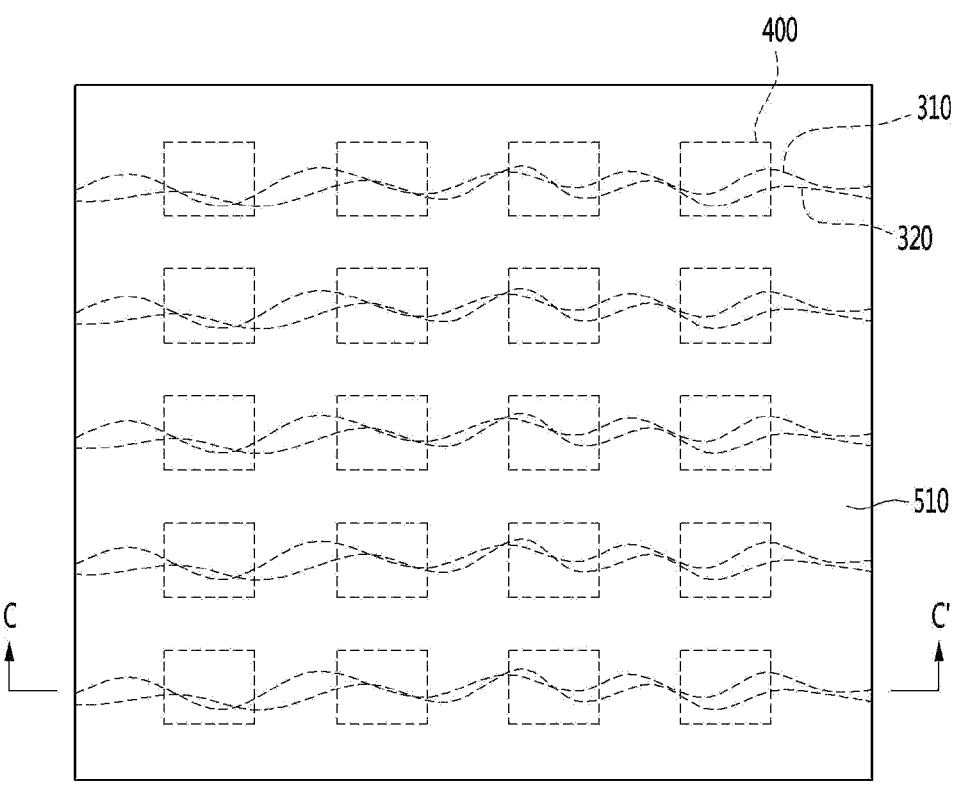
【FIG. 5】
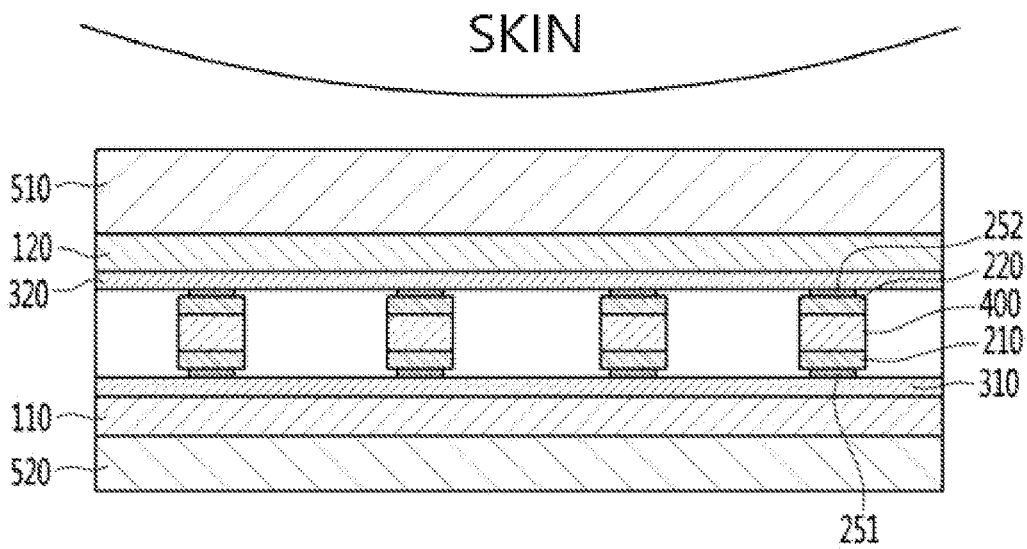

【FIG. 6】
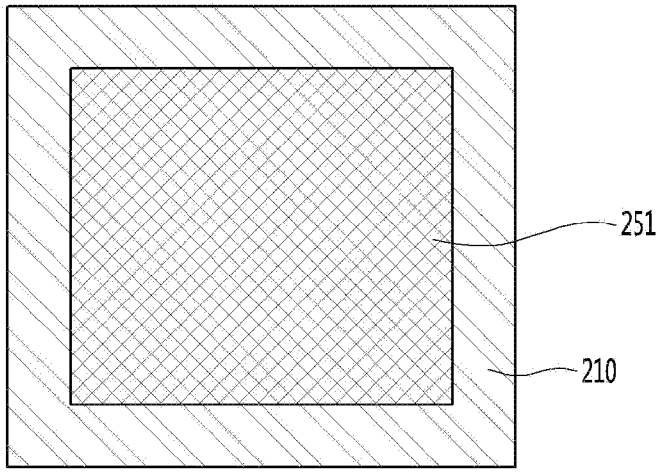
【FIG. 7】
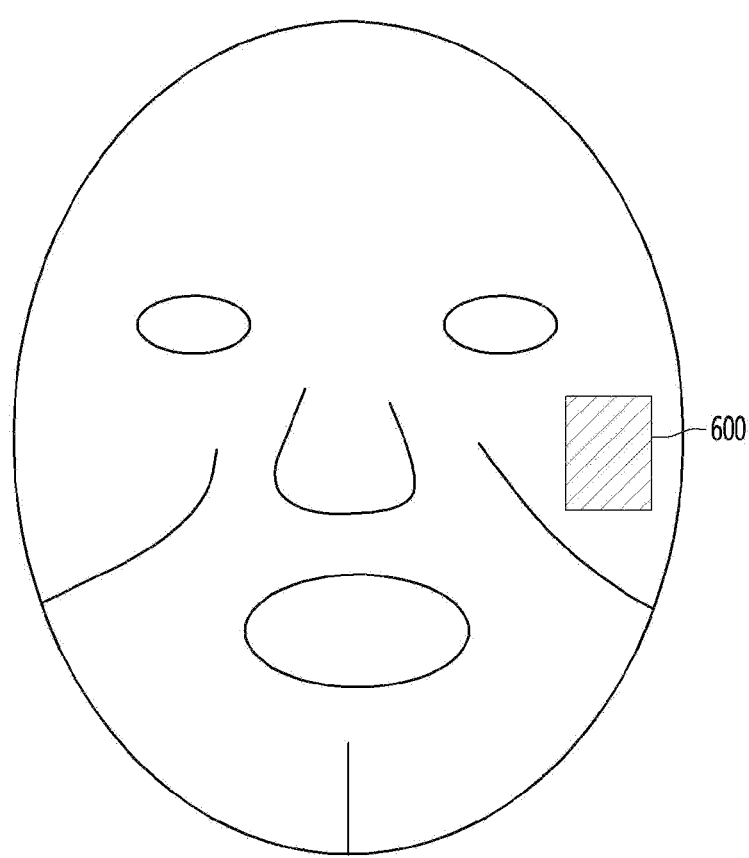

【FIG. 8】
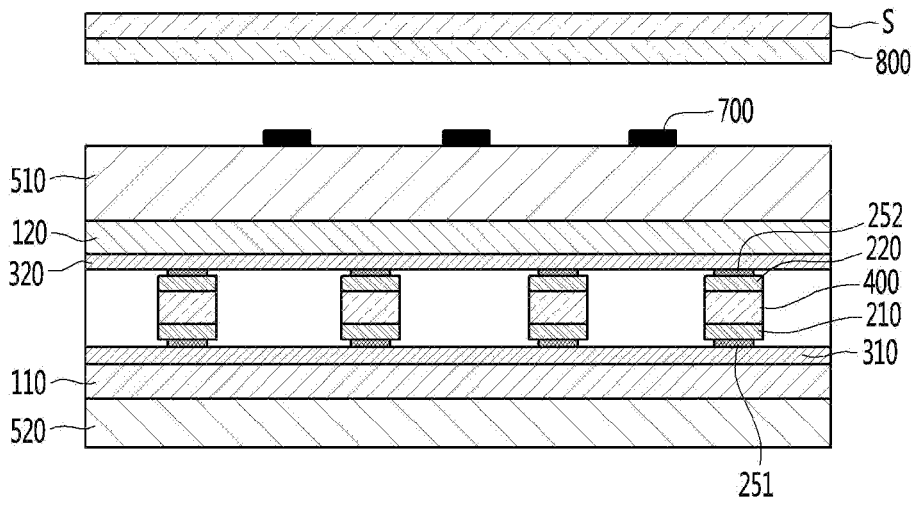
【FIG. 9】
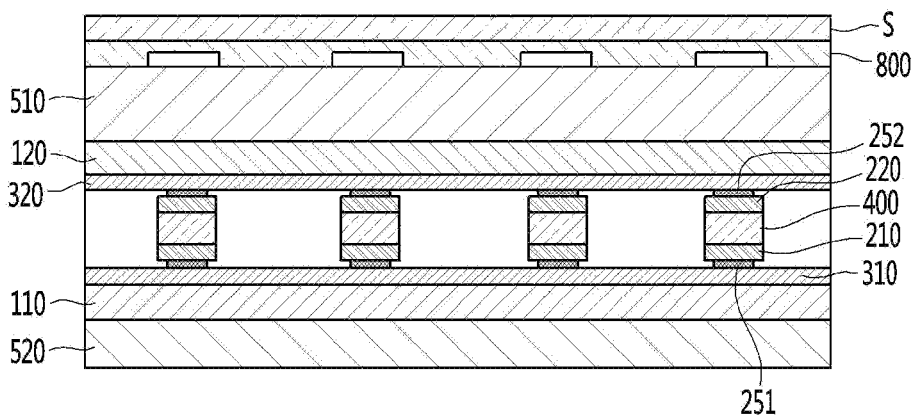

【FIG. 10】
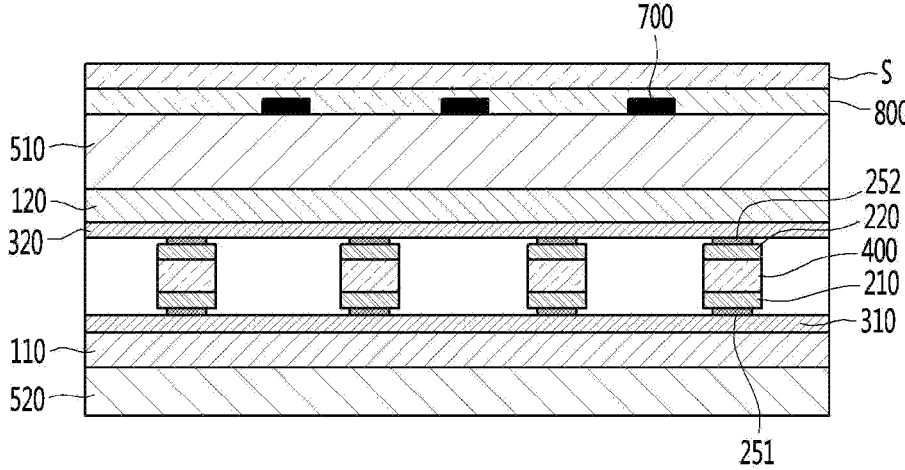
【FIG. 11】
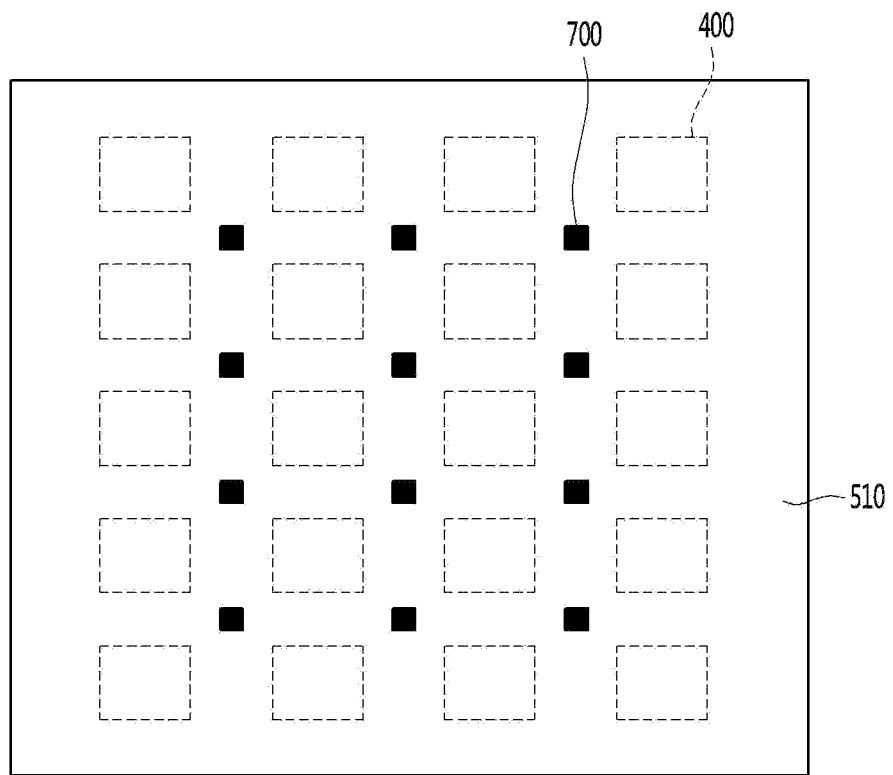

【FIG. 12】
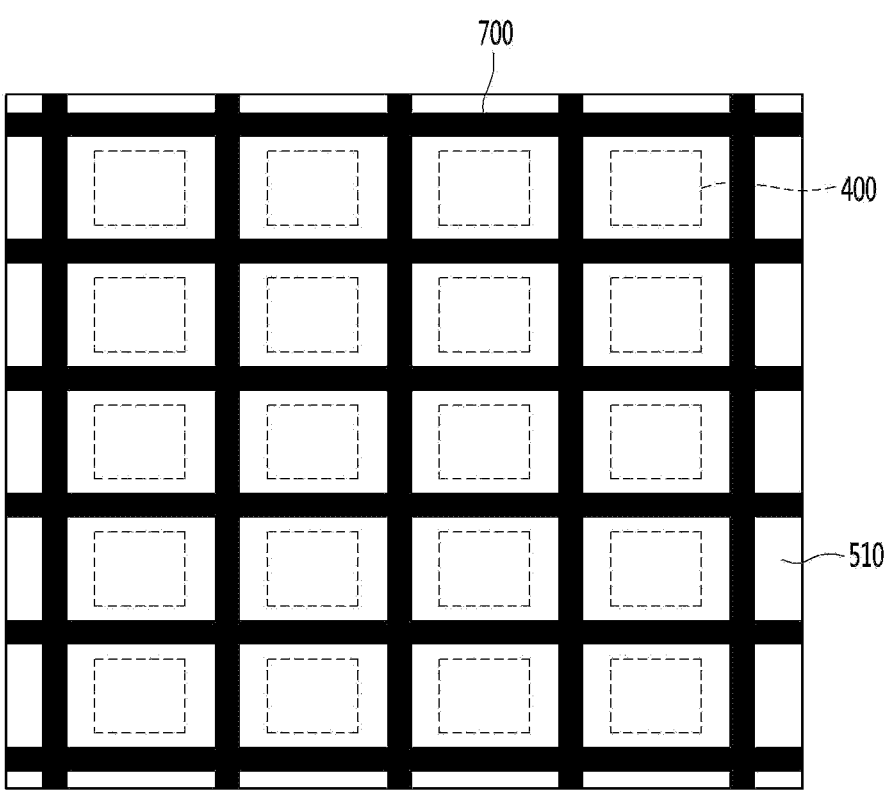

【FIG. 13】
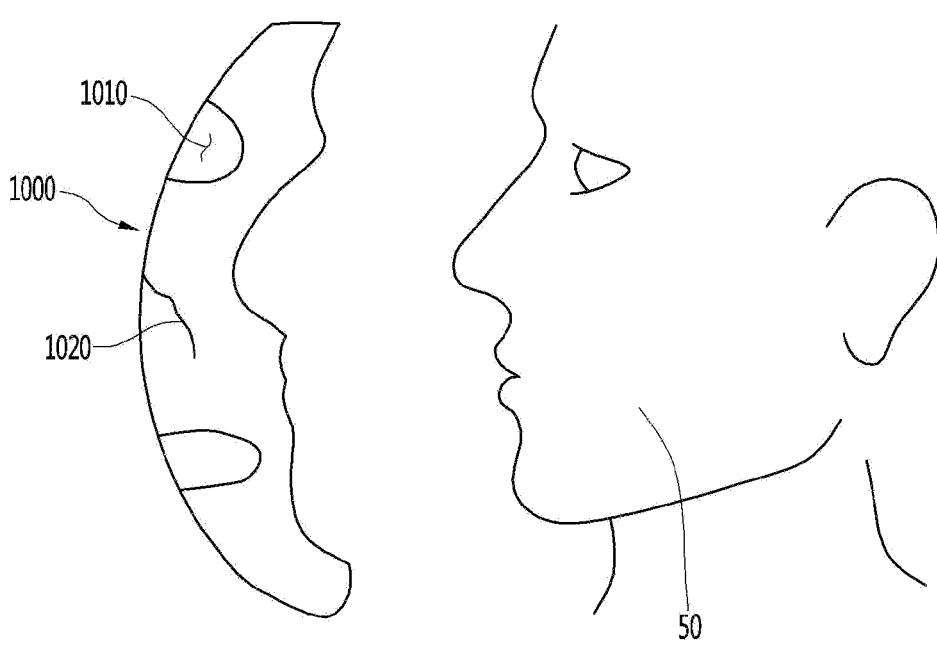

【FIG. 14】
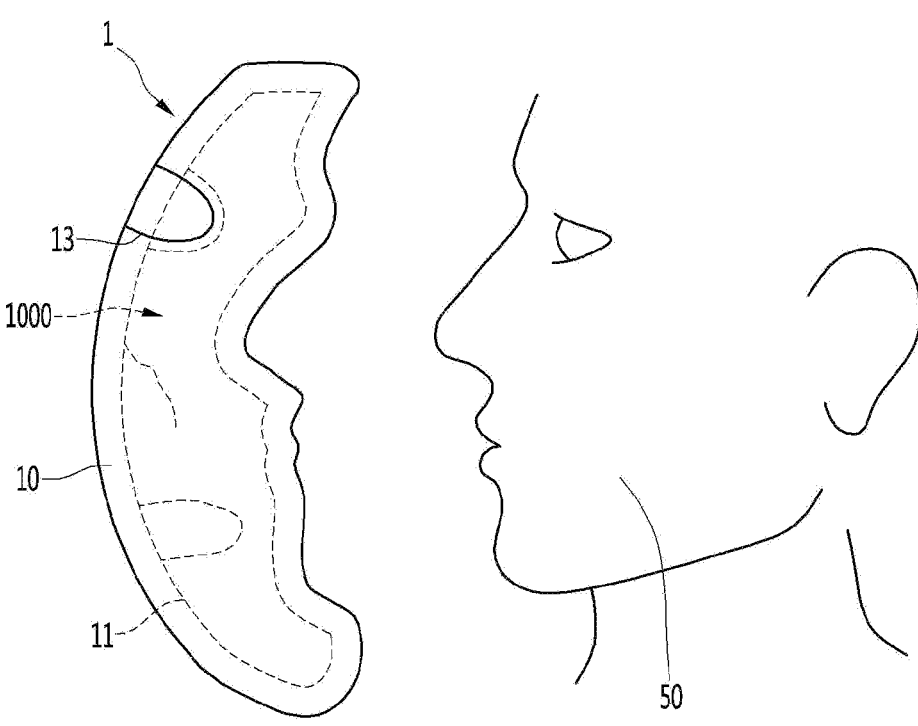

ULTRASONIC MASK AND SKIN CARE DEVICE COMPRISING SAME

CROSS-REFERENCE TO RELATED PATENT APPLICATIONS

This application is a U.S. National Stage Application under 35 U.S.C. § 371 of PCT Application No. PCT/KR2020/002713, filed Feb. 26, 2020, which claims priority to Korean Patent Application No. 10-2019-0027304, filed Mar. 11, 2019, whose entire disclosures are hereby incorporated by reference.

TECHNICAL FIELD

An embodiment relates to an ultrasonic mask that promotes beauty using an ultrasonic wave having a mid-frequency or low-frequency band of 1 MHz or less.

BACKGROUND ART

Human skin may be damaged or contaminated depending on external factors such as environmental pollution, ultra-violet rays, stress, and the like, and wrinkles may occur due to internal factors such as aging, hormonal changes, and the like. Recently, as interest in the skin has increased, various devices for skin treatment, beauty, and anti-aging have been developed.

In detail, a device has been developed, which is capable of applying thermal energy to the skin, for example, a device capable of improving skin elasticity by applying infrared energy. In addition, a device using sound waves or light rays has been developed in order to effectively inject cosmetics or drugs into the skin. For example, a device has been developed, which is capable of forming a path through which cosmetics or drugs are injected into the skin using sonophoresis and laserporation. In addition, a device using electric propulsion force has been developed in order to effectively inject cosmetics or drugs into the skin. For example, a device has been developed, which is capable of effectively injecting ionic substances contained in cosmetics or drugs into the skin using iontophoresis, electroporation, and electroosmosis. That is, various devices have been developed, which is capable of caring or treating a user's skin by providing light energy, microcurrent, vibration, or the like to the skin.

In general, the above-described devices may be provided in a form of a patch detachable to the skin, and the devices are attached to a specific skin region to care or treat the skin of the attached region. In addition, the above-described devices are provided in a form of a mask pack disposed to cover the entire user's face to care or treat the facial skin.

However, the devices have a problem that it is difficult to effectively adhere to curved skin surfaces such as both cheeks, nose, and the like. In detail, it may be difficult to effectively adhere to the user's skin due to materials and variable characteristics of the device. Accordingly, the device may be operated in a state in which the device is not completely adhered to the user's skin, and the device may be separated from the user's skin due to the user's movement or vibration of the device during the operation thereof.

In this case, there is a problem that it is difficult for the user to check whether the device is adhered to the skin, and thus, it is difficult to effectively obtain a care effect through the device.

Therefore, a new mask capable of solving the above-described problem is required.

DISCLOSURE

Technical Problem

An embodiment is to provide an ultrasonic mask capable of easily delivering a substance used for cosmetics or medical purposes to the skin of the human body.

Technical Solution

An ultrasonic mask according to an embodiment includes: a first substrate; a first wire disposed on an upper surface of the first substrate; a second substrate disposed above the first substrate; a second wire disposed on a lower surface of the second substrate; a piezoelectric member between the first substrate and the second substrate; a first electrode connected to the first wire and disposed on a lower surface of the piezoelectric member; and a second electrode connected to the second wire and disposed on an upper surface of the piezoelectric member, wherein the first wire and the second wire have a curvature (mm) of 5R to 15R, and the piezoelectric member generates an ultrasonic wave having a frequency band of 20 kHz to 1 MHz.

Advantageous Effects

The ultrasonic mask according to the embodiment may easily transfer a material into the skin of the human body using ultrasonic waves.

In detail, cosmetic substances such as cosmetics may be easily delivered according to a position, shape, and size of an object to be worn by a user through a rigid piezoelectric member, a flexible substrate, and a wire.

In addition, when the user wears the ultrasonic mask through the substrate and the wire that may be stretched, it is possible to prevent an electrode from being damaged due to deformation of the ultrasonic mask.

In addition, it is possible to minimize the loss of ultrasonic waves generated during transmission by controlling the directionality of the ultrasonic waves generated from the piezoelectric member by the matching layer and the backing layer.

In addition, it is possible to minimize the loss of ultrasonic waves generated during transmission by controlling thicknesses of the matching layer and the backing layer and controlling the movement of ultrasonic waves according to the frequency band of the ultrasonic waves generated from the piezoelectric member.

DESCRIPTION OF DRAWINGS

FIG. 1 is a top view of an ultrasonic mask according to an embodiment.

FIG. 2 is an enlarged top view of region A of FIG. 1.

FIG. 3 is a cross-sectional view taken along line B-B' of FIG. 2.

FIG. 4 is another enlarged top view of region A of FIG. 1.

FIG. 5 is a cross-sectional view taken along line C-C' of FIG. 4.

FIG. 6 is a view for describing an overlapping relationship between an adhesive layer and an electrode of an ultrasonic mask according to an embodiment.

FIG. 7 is another top view of the ultrasonic mask according to the embodiment.

FIG. 8 is another cross-sectional view taken along line C-C' of FIG. 4.

FIGS. 9 and 10 are views for describing the arrangement of cosmetic ingredients according to a spacer.

FIGS. 11 and 12 are views for describing a position of the spacer of the ultrasonic mask according to the embodiment.

FIGS. 13 and 14 are side views of an ultrasonic mask according to another embodiment.

MODES OF THE INVENTION

Hereinafter, embodiments of the present invention will be described in detail with reference to the accompanying drawings. However, the spirit and scope of the present invention is not limited to a part of the embodiments described, and may be implemented in various other forms, and within the spirit and scope of the present invention, one or more of the elements of the embodiments may be selectively combined and replaced.

In addition, unless expressly otherwise defined and described, the terms used in the embodiments of the present invention (including technical and scientific terms may be construed the same meaning as commonly understood by one of ordinary skill in the art to which this invention belongs, and the terms such as those defined in commonly used dictionaries may be interpreted as having a meaning that is consistent with their meaning in the context of the relevant art.

In addition, the terms used in the embodiments of the present invention are for describing the embodiments and are not intended to limit the present invention. In this specification, the singular forms may also include the plural forms unless specifically stated in the phrase, and may include at least one of all combinations that may be combined in A, B, and C when described in "at least one (or more) of A (and), B, and C".

Further, in describing the elements of the embodiments of the present invention, the terms such as first, second, A, B, (A, and (b) may be used. These terms are only used to distinguish the elements from other elements, and the terms are not limited to the essence, order, or order of the elements.

In addition, when an element is described as being "connected", "coupled", or "connected" to another element, it may include not only when the element is directly "connected" to, "coupled" to, or "connected" to other elements, but also when the element is "connected", "coupled", or "connected" by another element between the element and other elements.

Further, when described as being formed or disposed "on (over)" or "under (below)" of each element, the "on (over)" or "under (below)" may include not only when two elements are directly connected to each other, but also when one or more other elements are formed or disposed between two elements.

Furthermore, when expressed as "on (over)" or "under (below)", it may include not only the upper direction but also the lower direction based on one element.

Hereinafter, an ultrasonic mask according to embodiments will be described with reference to the drawings.

FIG. 1 is a view illustrating the ultrasonic mask according to the embodiment.

Referring to FIG. 1, an ultrasonic mask 1000 according to an embodiment may be formed to correspond to a shape of human face. In detail, the ultrasonic mask may have a shape corresponding to the shape of human face to deliver cosmetic ingredients such as cosmetics or drugs formed on one surface of the ultrasonic mask to the human facial skin.

The ultrasonic mask 1000 may be provided in a predetermined size to cover a user's face and may have a predetermined elasticity in order to be adhered to the user's face. The ultrasonic mask 1000 may include one surface in contact with a user's skin and the other surface opposite to the one surface, and the one surface of the ultrasonic mask 1000 may be made of a material that is harmless to the human body, so that it is harmless despite being in contact with the user's skin for a long time.

The ultrasonic mask 1000 may include an opening 1010 and/or a cutout portion 1020. In detail, the opening 1010 may be formed in a portion corresponding to the user's eyes or mouth. The opening 1010 is a region penetrating through one surface and the other surface of the mask 1000, and when the user wears the mask 1000, the user's eyes and mouth may be inserted into the opening 1010, and the region excluding the opening 1010 may be closely adhered to the user's face.

In addition, the cutout portion 1020 may be formed in a portion corresponding to both cheek lines, chin, and the like, which are relatively curved in order to improve adhesion between the mask 1000 and the skin. The cutout portion 1020 may have a form in which one surface and the other surface of the mask 1000 are partially cut.

The ultrasonic mask may be attached to a human face to deliver cosmetic ingredients such as cosmetics or drug substances to a human facial region with which the mask is in contact.

For example, the ultrasonic mask may be directly adhered to the skin of the human body, and cosmetic substances applied in advance to the skin may be easily delivered to the epidermal layer through the stratum corneum of the skin by ultrasonic waves generated from the ultrasonic mask.

That is, the ultrasonic mask forms a path through which a substance moves to the skin of the human body through ultrasonic waves, and thus, a substance to be absorbed into the skin may be easily delivered into the skin to be absorbed into the skin.

In detail, the mask according to the embodiment may deliver cosmetic substances or drug substances to a region of the human body that is in contact with the mask using a sonophoresis principle.

The sonophoresis principle is a means of delivering cosmetic ingredients or drug ingredients using ultrasonic waves. In detail, the sonophoresis principle is defined that microbubbles inside the skin are expanded by ultrasonic waves to form micro-channels in the skin so as to enable to absorb polar and non-polar particles and macromolecules within 5 μm.

That is, in the ultrasonic mask according to the embodiment, ultrasonic waves are applied in a direction of the skin of the human body by a piezoelectric member inside the mask, and ingredients such as cosmetic substances positioned on one surface of the ultrasonic mask facing the skin of the human body may pass through the stratum corneum of the skin through microchannels of the skin formed by the ultrasonic waves to be delivered to the epidermal layer.

Meanwhile, the ultrasonic mask according to the embodiment described below relates to an ultrasonic mask that may absorb ingredients such as cosmetic substances into the skin in a simple manner using a mask method, minimize the loss of ultrasonic waves to improve drug delivery efficiency, and minimize damage to electrodes inside the mask due to wearing the mask.

Hereinafter, the ultrasonic mask according to the embodiment will be described in detail through an internal structure of the mask according to the embodiment.

Referring to FIGS. 2 to 6, the ultrasonic mask according to the embodiment may include a substrate 100, an electrode 200, a wire 300, and a piezoelectric member 400.

The substrate 100 may serve to support the electrode 200, the wire 300, and the piezoelectric member 400.

The substrate 100 may include two substrates with the piezoelectric member interposed therebetween.

In detail, the substrate 100 may include a first substrate 110 and a second substrate 120. The first substrate 110 and the second substrate 120 may support the electrode 200, the wire 300, and the piezoelectric member 400, respectively. That is, the substrate 100 may be a supporting substrate supporting an electrode or the like.

For example, the first substrate 110 may be disposed while supporting the first electrode 210 and the first wire 310, and the second substrate 120 may be disposed while supporting a second electrode 220 and a second wire 320.

That is, the first substrate 110 and the second substrate 120 may be spaced apart from each other and support each of the electrodes and wire, and a separate adhesive material may be disposed between the first substrate 110 and the second substrate 120 to be adhered to each other and disposed.

The first substrate 110 and the second substrate 120 may be flexible. In detail, the first substrate 110 and the second substrate 120 may be flexible so as to be bendable or foldable. In addition, at least one of the first substrate 110 and the second substrate 120 is closely adhered to the human face described above, and thus the substrate may be formed of a material harmless to the human body.

For example, the first substrate 110 and the second substrate 120 may include plastic. As an example, the first substrate 110 and the second substrate 120 may include a flexible plastic such as polyimide (PI), polyethylene terephthalate (PET), propylene glycol (PPG) polycarbonate (PC), or the like Accordingly, when the user wears the ultrasonic mask on the face or the like and deforms the ultrasonic mask according to the size and shape of the user's face, the ultrasonic mask may be easily stretched.

In addition, the substrate 100 may have a certain thickness.

For example, the substrate 100 may have a thickness of about 0.5 μm to about 5 μm or less. When the thickness of the substrate 100 is less than about 0.5 μm, a shape of the region of the substrate 100 overlapping the components is changed by the weight of components to be disposed on the substrate 100, for example, the piezoelectric member 400, so that a problem that may affect adhesion and absorption of cosmetic ingredients may occur. Accordingly, reliability of the substrate 100 may be deteriorated, and an alignment tolerance of components disposed on the substrate 100 may be increased.

In addition, when the thickness of the substrate 100 exceeds about 5 μm, the overall thickness of the mask 1000 may be increased. Accordingly, there is a problem that the mask 1000 may not be efficiently varied according to the shape of the user's skin, and thus the mask 1000 does not effectively adhere to the user's skin.

Preferably, the substrate 100 may have a thickness of about 0.5 μm to about 3 μm. When the thickness of the substrate 100 satisfies the above-described range, the substrate 100 may be efficiently varied in a form corresponding to the user's skin and the overall thickness and weight of the mask 1000 may be reduced while maintaining reliability and alignment characteristics.

The electrode 200 may include the first electrode 210 and the second electrode 220 disposed on the substrate.

The first electrode 210 may be disposed on the first substrate 110, and the second electrode 220 may be disposed on the second substrate 120. The first electrode 210 and the second electrode 220 may be in contact with the piezoelectric member 400.

In detail, the first electrode 210 may be disposed in contact with one surface of the piezoelectric member 400, and the second electrode 220 may be disposed in contact with the other surface opposite to the one surface of the piezoelectric member 400.

Accordingly, the first electrode 210 and the second electrode 220 may be disposed on both surfaces of the piezoelectric member 400, respectively, and a voltage may be applied to the piezoelectric member by the first electrode 210 and the second electrode 220 A to vibrate the piezoelectric member.

In detail, a voltage applied from the outside of the ultrasonic mask is transmitted to the first electrode 210 and the second electrode 220 through wire, and accordingly, the voltage is applied to the piezoelectric member, so that the piezoelectric member may be vibrated to generate ultrasonic waves having a specific frequency range.

As an example, the first electrode 210 and the second electrode 220 may be disposed on an upper surface and a lower surface of the piezoelectric member 400, respectively.

The first electrode 210 may be disposed on the entire surface of one surface of the piezoelectric member 400. In addition, the second electrode 220 may be disposed on the entire surface of the other surface of the piezoelectric member 400. In this case, the entire surface of one surface and the other surface of the piezoelectric member may be defined as a region including an error during the process.

At least one of the first electrode 210 and the second electrode 220 may include various metals. For example, at least one of the first electrode 210 and the second electrode 220 may include at least one metal of chromium (Cr), nickel (Ni), copper (Cu), aluminum (Al), silver (Ag), molybdenum (Mo), gold (Au), titanium (Ti), and alloys thereof.

Alternatively, at least one of the first electrode 210 and the second electrode 220 may be formed in a mesh shape. In detail, at least one of the first electrode 210 and the second electrode 220 may include a plurality of sub-electrodes, and the sub-electrodes may be disposed to cross each other in the mesh shape.

In detail, at least one of the first electrode 210 and the second electrode 220 may include a mesh line LA and a mesh opening OA between the mesh lines LA by the plurality of sub-electrodes crossing each other in the mesh shape.

A line width of the mesh line LA may be about 0.1 μm to about 10 μm. A mesh line having a line width of less than about 0.1 μm of the mesh line LA may not be possible in a manufacturing process, and when the line width exceeds about 10 μm, an electrode pattern may be visually recognized from the outside and visibility may be reduced. In detail, the line width of the mesh line LA may be about 1 μm to about 5 μm. In more detail, the line width of the mesh line LA may be about 1.5 μm to about 3 μm.

In addition, the thickness of the mesh line LA may be about 100 nm to about 1000 nm. When the thickness of the mesh line is less than about 100 nm, an electrode resistance may increase and electrical characteristics may be deteriorated. When the thickness of the mesh line exceeds about 1000 nm, the overall thickness of the ultrasonic mask may increase and process efficiency may be deteriorated. In detail, the thickness of the mesh line LA may be about 150 nm to about 500 nm. In more detail, the thickness of the mesh line LA may be about 180 nm to about 200 nm.

In addition, the mesh opening may be formed in various shapes. For example, the mesh opening OA may have various shapes such as a square shape, a diamond shape, a polygonal shape of pentagonal shape and hexagonal shape, a circular shape, or the like. In addition, the mesh opening may be formed in a regular shape or a random shape.

Referring to FIGS. 2 and 3, the first electrode 210 and the second electrode 220 may be disposed to extend in different directions. For example, the first electrode 210 may be disposed to extend in a first direction, and the second electrode 220 may be disposed to extend in a second direction different from the first direction. For example, the first electrode 210 and the second electrode 220 may be disposed to extend in a direction crossing each other.

Alternatively, referring to FIGS. 4 and 5, the first electrode 210 and the second electrode 220 may be disposed to extend in the same direction. For example, the first electrode 210 may be disposed to extend in the first direction or the second direction.

For example, the first electrode 210 and the second electrode 220 may be disposed to extend in the same direction to each other so as to vertically overlap or not overlap each other.

The piezoelectric member 400 may be disposed between the first substrate 110 and the second substrate 120. In detail, a plurality of piezoelectric members 400 for generating ultrasonic waves may be disposed between the first substrate 110 and the second substrate 120. The plurality of piezoelectric members 400 may be disposed to be spaced apart from each other between the first and second substrates 110 and 120 to generate the ultrasonic waves over the entire area of the ultrasonic mask.

Meanwhile, the piezoelectric members 400 may be disposed to be spaced apart at the same or a similar distance on the substrate.

Alternatively, the piezoelectric members 400 may be disposed to be spaced apart from each other at different distances on the substrate. For example, when the ultrasonic mask is put on the skin of the human body, the separation distance of the piezoelectric member 400 may vary depending on a size at which the ultrasonic mask is bent.

For example, when the ultrasonic mask is put on the skin of the human body, a bent region for each region may vary depending on the shape and size of the face. In this case, the distance of the piezoelectric member 400 may be increased in the region where the ultrasonic mask is bent, and accordingly, the distance of the piezoelectric member 400 is decreased in a region that is largely bent, so that it is possible to compensate that the distance of the piezoelectric element is varied for each region when the ultrasonic mask is put on the skin. That is, the distance between the piezoelectric members 400 may be decreased in a region having a large curvature and may be relatively increased in a region having a small curvature.

The piezoelectric member 400 may include a rigid material.

The piezoelectric member 400 may include various piezoelectric materials. For example, the piezoelectric member 400 may include single crystal ceramics, polycrystalline ceramics, a polymer material, a thin film material, or a composite material in which the polycrystalline material and the polymer material are composited.

A piezoelectric material of the single crystal ceramics may include $\alpha$-AlPO$_4$, $\alpha$-SiO2, LiTiO3, LiNbO3, SrxBayNb2O3, Pb5-Ge3O11, Tb2(MnO4)3, Li2B4O7, CdS, ZnO, Bi12SiO20, or Bi12GeO20.

In addition, a piezoelectric material of the polycrystalline ceramics may include PZT-based, PT-based, PZT-Complex Perovskite-based, or BaTiO3.

In addition, a piezoelectric material of the polymer material may include PVDF, P(VDF-TrFe), P(VDFTeFE), or TGS.

In addition, a piezoelectric material of the thin film material may include ZnO, CdS, or AlN.

In addition, a piezoelectric material of the composite material may include PZT-PVDF, PZT-Silicon Rubber, PZT-Epoxy, PZT-foaming polymer, or PZT-foaming urethane.

The plurality of piezoelectric members 400 may include at least one piezoelectric material among the single crystal ceramics, the polycrystalline ceramics, the polymer material, the thin film material, or the composite material in which the polycrystalline material and the polymer material are composited.

The plurality of piezoelectric members 400 may include the same piezoelectric material or may include different piezoelectric materials.

For example, the ultrasonic mask according to the embodiment may include a piezoelectric material that generates low-frequency or medium-frequency ultrasonic waves. In detail, the ultrasonic mask according to the embodiment may include a piezoelectric material that generates ultrasonic waves of a low frequency having a 20 kHz to 100 kHz band and/or a medium frequency having a 100 kHz to 1 MHz band that are optimized for beauty.

As an example, the ultrasonic mask according to the embodiment may include single crystal or polycrystalline ceramics including ceramic.

The waveform of the ultrasonic wave applied from the piezoelectric member 400 is not limited and may include a sine waveform, a sawtooth waveform, or a pulse waveform.

In addition, ultrasonic waves generated from the piezoelectric member 400 may be applied as at least one of a transverse wave and a longitudinal wave. In detail, the ultrasonic waves generated from the piezoelectric member 400 may be applied as a single wave of a transverse wave, a single wave of a longitudinal wave, or a plurality of waves applied with both transverse wave and longitudinal wave.

That is, the piezoelectric member according to the embodiment may generate the ultrasonic waves in a single or multiple resonance modes.

A thickness of the piezoelectric member 400 may be about 600 μm or less. In detail, the thickness of the piezoelectric member 400 may be about 500 μm or less. Preferably, the thickness of the piezoelectric member 400 may be about 300 μm or less. It is preferable that the thickness of the piezoelectric member 400 satisfies the above-described range in consideration of the variable characteristics of the ultrasonic mask 1000.

The piezoelectric member 400 may have various shapes. For example, the piezoelectric member 400 may have a polygonal column shape in which lower and upper surfaces are polygonal, and the lower and upper surfaces may have a circular column shape. In addition, one surface of the lower and upper surfaces of the piezoelectric member 400 may be a polygon and the other surface may have a pillar shape. As an example, an area of at least one of the lower surface and the upper surface of the piezoelectric member 400 may be about 100 mm² or less.

As described above, the piezoelectric member 400 may have various pillar shapes, and intensity of ultrasonic vibration and an oscillation direction of vibration generated according to the pillar shape may be controlled. In addition, the intensity of vibration transmitted to the user's skin may be adjusted according to a size, arrangement interval, arrangement density, and the like of the piezoelectric member 400.

The piezoelectric member 400 may generate various waves. For example, the piezoelectric member 400 may generate at least one wave of a transverse wave in which a traveling direction of wave and a vibration direction of medium are perpendicular, and a longitudinal wave in which the traveling direction of wave and the vibration direction of medium are the same. In addition, the piezoelectric member 400 may multiple-resonate.

For example, the piezoelectric member 400 may include at least one via hole and may multiple-resonate by the formed via holes. In this case, an upper area of the via holes may be about 10% to about 45% of an area of the upper surface of the piezoelectric member 400 for multiple resonance.

In addition, when the piezoelectric member 400 multiple-resonates by the via holes, the number of multiple resonance frequency regions may correspond to the number of the via holes. That is, the piezoelectric member 400 may emit wavelengths of various frequency ranges as the number of the via holes increases in a set number range of via holes.

The wire may include the first wire 310 and the second wire 320 disposed on the substrate.

The first wire 310 may be disposed on the first substrate 110, and the second wire 320 may be disposed on the second substrate 120.

The first wire 310 and the second wire 320 may include a material the same as or similar to that of the first electrode 210 and the second electrode 220 described above.

The first wire 310 and the second wire 320 may include a flexible material.

For example, at least one of the first wire 310 and the second wire 320 may include various metals. At least one of the first wire 310 and the second wire 320 may include at least one metal of chromium (Cr), nickel (Ni), copper (Cu), aluminum (Al), silver (Ag), molybdenum (Mo), gold (Au), titanium (Ti), and alloys thereof.

The first wire 310 and the second wire 320 may electrically connect the plurality of piezoelectric members 400 disposed to be spaced apart from each other between the first substrate 110 and the second substrate 120. That is, the first wire 310 and the second wire 320 may be disposed to extend in an extension direction of the piezoelectric members spaced apart from each other, and accordingly, the plurality of piezoelectric members 400 may be electrically connected by the first wire 310 and the second wire 320.

In addition, the first wire 310 and the second wire 320 may be connected to the electrode.

In detail, the first wire 310 may be electrically connected to the first electrode 210, and the second wire 320 may be electrically connected to the second electrode 220.

In detail, the first electrode 210 and the first wire 310 may be connected through a first adhesive layer 251, and the second electrode 220 and the second wire 320 may be connected to a second adhesive layer 252.

That is, the first adhesive layer 251 is disposed between the first electrode 210 and the first wire 310, so that the first electrode 210 and the first wire 310 may be in contact with each other. In addition, the second adhesive layer 252 is disposed between the second electrode 220 and the second wire 320 so that the second electrode 220 and the first wire 320 may be in contact with each other.

The first adhesive layer 251 and the second adhesive layer 252 may have conductivity. In detail, the first adhesive layer 251 and the second adhesive layer 252 may be conductive pastes. For example, the first adhesive layer 251 and the second adhesive layer 252 may include silver (Ag) paste.

Accordingly, the first electrode 210 and the first wire 310 and the second electrode 220 and the second wire 320 may be electrically connected to by the first adhesive layer 251 and the second adhesive layer 252.

Meanwhile, the first adhesive layer 251 and the second adhesive layer 252 may be formed to have the same and similar thickness. Alternatively, the first adhesive layer 251 and the second adhesive layer 252 may be formed to have different thicknesses.

In detail, a thickness of the first adhesive layer 251 may be greater than a thickness of the second adhesive layer 252. That is, the thickness of the first adhesive layer 251 disposed further from the skin may be greater than the thickness of the second adhesive layer 252.

Alternatively, the first adhesive layer 251 may include a first-first adhesive layer and a first-second adhesive layer. In detail, the first-first adhesive layer may be disposed above the first substrate 110 and the first-second adhesive layer may be disposed below the first substrate 110 based on the first substrate 110.

For example, the first-first adhesive layer may be disposed between the first electrode 210 and the first wire 310, and the first-second adhesive layer may be disposed between the second base layer 520 and the first substrates 110.

Accordingly, ultrasonic waves generated from the piezoelectric member 400 and moved in a opposite direction of the skin may be reflected by the second adhesive layer 252 to transmit in a direction of the skin by making a thickness of the first adhesive layer different from a thickness of the second adhesive layer, thereby minimizing the loss of ultrasonic waves.

Meanwhile, referring to FIG. 6, the first adhesive layer 251 and the second adhesive layer 252 are disposed in a region overlapping one surface of the first electrode and the second electrode.

One surface of the first electrode and the second electrode may be greater than or equal to one surface of the first adhesive layer 251 and the second adhesive layer 252. That is, a contact area between the electrode and the adhesive layer may be smaller than that of one surface of the electrode.

When a region where one surface of the first adhesive layer 251 and the first electrode 210 overlap is defined as a first overlapping region, and a region where the second adhesive layer 252 and the other surface of the second electrode 220 overlap is defined as a second overlapping region, an overlapping area of the first overlapping region and the second overlapping region may be about 20% or more of the entire area of the first electrode 210 or the second electrode 220. In detail, the overlapping area of the first overlapping region and the second overlapping region may be about 20% to about 100% of the entire area of the first electrode 210 or the second electrode 220.

When the overlapping area of the first overlapping region and the second overlapping region is less than about 20% of the entire area of the first electrode 210 or the second electrode 220, electrical characteristics of the wire connected to the first electrode 210 or the second electrode 220 may be deteriorated, and thus reliability of the ultrasonic mask may be deteriorated.

That is, the first adhesive layer 251 and the first electrode 210 and the second adhesive layer 252 and the second electrode 220 may completely overlap and be adhered to each other, or the first adhesive layer 251 and the second adhesive layer 252 may be in contact with each other while exposing one surface of the first electrode 210 or the second electrode 220.

In addition, overlapping areas of the first overlapping region and the second overlapping region of the adhesive layer disposed on a plurality of electrodes may have a uniform size. For example, a difference between the overlapping areas of the first overlapping region and the second overlapping region of the adhesive layer disposed on the plurality of electrodes may be about 10% or less. In detail, the difference between the overlapping areas of the first overlapping region and the second overlapping region of the adhesive layer disposed on the plurality of electrodes may be 5% to 10%. Accordingly, the ultrasonic waves generated from the plurality of piezoelectric members 400 may be transmitted in a uniform size to each area of the ultrasonic mask by minimizing the difference between the overlapping areas of the first overlapping region and the second overlapping region.

Meanwhile, the first wire 310 and the second wire 320 connecting the plurality of piezoelectric members 400 may be stretched in one direction. That is, lengths of the first wire 310 and the second wire 320 may increase or decrease according to an external force.

In addition, the first wire 310 and the second wire 320 may be formed while having a curvature. In detail, the first wire 310 and the second wire 320 may have a shape in which the same or similar curved pattern is repeated.

For example, the first wire 310 and the second wire 320 may have a curvature of 5R to 15R (mm) and an elongation of about 10% to 50%.

In addition, the first wire 310 and the second wire 320 may have a predetermined thickness and line width. For example, a line width of the first wire 310 and the second wire 320 may be 50 μm to 500 μm. In addition, the thickness of the first wire 310 and the second wire 320 may have a size of about 1/10 or less of the line width. As an example, the thickness of the first wire 310 and the second wire 320 may be about 5 μm to 50 μm.

Accordingly, when the ultrasonic mask is bent or folded in one direction, it is possible to prevent the wires from being disconnected or damaged by controlling the line width and thickness of the first wire 310 and the second wire 320, thereby improving the reliability of the mask.

When the user wears the ultrasonic mask applied to the human face or the like, the ultrasonic mask may be pulled and fixed to each user's face according to a different shape and size of the human body for each user. Accordingly, when the user stretches the ultrasonic mask, it is possible to prevent the wires from being disconnected by forming the wire so that a curved shape having a certain curvature is repeated, thereby improving the reliability of the ultrasonic mask.

Meanwhile, a length of the first wire 310 and the second wire 320 disposed between the piezoelectric members 400 may be formed longer than a distance between the piezoelectric members 400. That is, the length of the first wire 310 and the second wire 320 formed while having a constant curvature size may be formed longer than the distance between the piezoelectric members 400.

Accordingly, when the ultrasonic mask 1000 is stretched, the length of the wire may be controlled together, so that it is possible to minimize a reliability failure due to disconnection of the wire.

Meanwhile, base layers for easily transmitting ultrasonic waves to the skin may be disposed on outer surfaces of the first substrate 110 and the second substrate 120, respectively.

The above-described substrates, wires, electrodes, and piezoelectric members may be disposed between the base layers, that is, the base layers may be support layers supporting a plurality of components.

For example, when it is defined that a position where the second substrate 120 is disposed is a place close to the skin of the human body, and a position where the first substrate 110 is disposed is a place far from the skin of the human body, a first base layer 510 in which the ultrasonic waves generated from the piezoelectric member 400 may be easily transmitted in the direction of the skin of the human body may be disposed on the outer surface of the second substrate 120. In addition, a second base layer 520 in which the ultrasonic waves generated from the piezoelectric member 400 are reflected so as to transmit ultrasonic waves in the direction of the skin of the human body may be disposed on the outer surface of the first substrate 110. That is, the first base layer 510 may be defined as a layer that is in direct contact with the skin of the human body and transmits ultrasonic waves.

Here, the outer surface of the first substrate 110 and the second substrate 120 may be defined as a surface opposite to the surface of the first substrate 110 and the second substrate 120 facing the piezoelectric member.

In detail, the first base layer 510 may be disposed on the outer surface of the second substrate 120. The first base layer 510 may include a matching layer.

The first base layer 510 may reduce energy loss due to reflection of an ultrasonic signal due to a difference in acoustic impedance between the piezoelectric member and the object, that is, the skin of the human body. To this end, the first base layer 510 is formed of a material having an acoustic impedance corresponding to between the acoustic impedance of the piezoelectric member and the acoustic impedance of the skin of the human body, and accordingly, energy loss of the ultrasonic signal may be minimized by configuring a plurality of acoustic matching layers having an acoustic impedance gradually decreasing from the first base layer 510 adjacent to the piezoelectric element.

As an example, the first base layer 510 may include silicon (Si). For example, the first base layer 510 may include silicon or a silicon compound. In addition, a thickness of the first base layer 510 may be about 1 mm or less. In detail, a thickness of the matching layer may be about 300 μm to about 1 mm.

The thickness of the first base layer 510 may be changed depending on the frequency of ultrasonic waves generated from the piezoelectric member 400.

In detail, the thickness of the first base layer 510 may be defined as a size of λ/4 or more of the wavelength at the wavelength λ calculated by the following equation.

$$\text{Sound velocity of the first base layer} = \text{Frequency generated from the piezoelectric member} \times \text{wavelength}(\lambda) \qquad \text{[Equation]}$$

That is, the thickness of the first base layer 510 may be formed so as to have a size of about 25% or more of the size of the wavelength calculated by the equation.

For example, when the first base layer includes silicon (Si), a wavelength value may be determined depending on a size of the frequency region generated in the piezoelectric member, and the thickness of the first base layer may be formed in a size of about 25% or more of the size of the wavelength.

Accordingly, when ultrasonic waves generated from the piezoelectric member are transmitted to the human skin by the matching layer, the loss of ultrasonic waves may be minimized.

The second base layer 520 may be disposed on the outer surface of the first substrate 110. The second base layer 520 may include a backing layer.

The second base layer 520 may reflect the ultrasonic waves generated from the piezoelectric member and moving in a direction of the second substrate that is a direction opposite to the skin of the human body in the direction of the skin of the human body. That is, the second base layer 520 may be a reflective layer that reflects the ultrasonic waves.

The backing layer may include a material the same as or similar to that of the matching layer. For example, the backing layer may include silicon (Si).

The backing layer may be formed with a thickness different from that of the matching layer. In detail, the backing layer may be formed to have the same or smaller thickness than that of the matching layer.

In addition, the second base layer 520 may have an air layer formed therein to easily reflect the ultrasonic waves. That is, a plurality of pores may be formed inside the second base layer 520 to reflect the ultrasonic waves incident into the second base layer 520 toward the first base layer 510.

In addition, the second base layer 520 may be formed in a shape different from that of the first base layer 510. In detail, the second base layer 520 may include a groove formed in a region corresponding to the piezoelectric member 400. Accordingly, the ultrasonic waves incident into the second base layer 520 may be reflected toward the first base layer 510 by the air layer formed inside the groove.

The first base layer 510 and the second base layer 520 may be formed to have a size the same as or similar to that of the first base layer 110 and the second base layer 120. That is, the first base layer 510 and the second base layer 520 may be disposed while covering the plurality of piezoelectric members.

That is, the first base layer 510 and the second base layer 520 are formed to be greater than an area of the piezoelectric member, so that ultrasonic waves radiated from the piezoelectric member may be effectively transmitted in the direction of the skin of the human body.

Accordingly, the ultrasonic waves generated radially from the piezoelectric material may be easily transmitted in the direction of the skin of the human body by the first base layer and the second base layer.

Meanwhile, a protective layer 150 may be disposed between the first substrate 110 and the second substrate 120. The protective layer 150 may include a material that is the same as or similar to that of at least one of the first base layer 510 and the second base layer 520. For example, the protective layer 150 may include silicon or a silicon-based compound.

The protective layer 150 prevents damage from external impacts or impurities to the piezoelectric member, the electrodes, the wires, and the like between the first substrate 110 and the second substrate 120, thereby improving the reliability of the ultrasonic mask.

The ultrasonic mask according to the embodiment may easily transfer a material into the skin of the human body using ultrasonic waves.

In detail, cosmetic substances such as cosmetics may be easily delivered according to a position, shape, and size of an object to be worn by a user through a rigid piezoelectric member, a flexible substrate, and a wire.

In addition, when the user wears the ultrasonic mask through the substrate and the wire that may be stretched, it is possible to prevent an electrode from being damaged due to deformation of the ultrasonic mask.

In addition, it is possible to minimize the loss of ultrasonic waves generated during transmission by controlling the directionality of the ultrasonic waves generated from the piezoelectric member by the matching layer and the backing layer.

In addition, it is possible to minimize the loss of ultrasonic waves generated during transmission by controlling thicknesses of the matching layer and the backing layer and controlling the movement of ultrasonic waves according to the frequency band of the ultrasonic waves generated from the piezoelectric member.

Referring to FIG. 7, the ultrasonic mask according to the embodiment may include an indicator. In detail, an indicator 600 capable of identifying an operating state of the ultrasonic mask may be disposed in one region of the ultrasonic mask.

The indicator 600 may be disposed on an outer surface of the ultrasonic mask so that the user may identify the indicator from the outside. That is, the ultrasonic mask may be formed on a surface opposite to a surface on which substances such as cosmetics, and the like are disposed.

The indicator 600 may display various operating states of the ultrasonic mask. For example, the indicator 600 may display the start/end of the ultrasonic mask. Further, the indicator 600 may display a frequency band generated by the ultrasonic mask.

The indicator 600 may include at least one of members capable of transmitting information to a user visually or aurally such as an LED, a display, and a buzzer.

The indicator 600 may be disposed outside the mask 1000 to display an operation state of the mask 1000. As an example, the indicator 600 may provide information on the start of the operation of the mask 1000, information indicating that the operation is in progress, and information on the completion of the operation through auditory information generated from a buzzer. In addition, the indicator 600 may display the operation state according to the emission color of the LED. In addition, the indicator may display information on an operating frequency region through the display.

In addition, the indicator 600 may provide information on whether the mask 1000 is closely adhered to the skin.

Referring to FIGS. 8 to 12, the ultrasonic mask according to the embodiment may include a plurality of spacers 700 disposed on the base layer.

In detail, the ultrasonic mask according to the embodiment may include the plurality of spacers 700 disposed on the first base layer, that is, the matching layer.

The plurality of spacers 700 may be disposed to be spaced apart from each other. For example, each of the spacers 700 may be disposed so as not to overlap a region where the piezoelectric member is disposed. In detail, each of the spacers 700 may be disposed so as not to overlap the region where the piezoelectric member is disposed so as not to affect the movement of the piezoelectric member to which ultrasonic waves generated from the piezoelectric member are transmitted.

The spacer 700 may be disposed on the matching layer to which a cosmetic ingredient 800 including cosmetics or drug substances applied to the skin S of the human body is applied to prevent the cosmetic substances or drug substances from being aggregated in one region.

In detail, referring to FIG. 9, when the ultrasonic mask is in contact with a material such as cosmetics applied to the skin, the material such as cosmetics moves outward form the region where the piezoelectric member is disposed by vibration and pressure generated from the piezoelectric member, so that a step may be formed.

Accordingly, an amount of the cosmetic substance is reduced in the region where the piezoelectric member is disposed, and thus the efficiency of movement of the cosmetic substance through ultrasonic waves may be deteriorated.

Accordingly, by disposing the plurality of spacers 700 between regions in which the piezoelectric member is disposed as shown in FIG. 10, the cosmetic substances, and the like are moved to the outside when the ultrasonic mask is in contact with the skin, and thus it is possible to prevent the amount of the cosmetic substances, and the like from being reduced in a region overlapping the piezoelectric member.

Referring to FIGS. 11 and 12, the spacers 700 may be disposed to be spaced apart in a dot shape between the piezoelectric members 400 as shown in FIG. 11 or may be formed in a linear shape connected to each other between the piezoelectric members 400 as shown in FIG. 12.

In the ultrasonic mask according to the embodiment, a plurality of spacers spaced apart from each other are disposed in a region not overlapping the piezoelectric member, and the ultrasonic mask is in contact with the skin, and then it is possible to prevent the cosmetic material from being aggregated into one region by vibration and pressure generated from the piezoelectric member.

Therefore, it is possible to improve the efficiency of transmitting cosmetic substances of the ultrasonic mask according to the embodiment.

FIG. 13 is a view illustrating a user wearing a mask according to an embodiment, and FIG. 14 is a view illustrating a skin care device to which the mask according to the embodiment is applied.

Referring to FIG. 13, the user may wear the ultrasonic mask 1000. The ultrasonic mask 1000 may include the above-described opening 1010, and the user may secure a view through the opening 1010. In addition, the mask 1000 may include the above-described cutout portion 1020, and the ultrasonic mask 1000 may be effectively close-adhered to the curved skin by the cutout portion 1020. In this case, one surface of the first base layer 510 may be in direct contact with the user's skin.

The ultrasonic mask 1000 may be operated by receiving power through an external power connected to the ultrasonic mask 1000. In addition, the ultrasonic mask 1000 may be operated by receiving power through a power supply unit (not shown) disposed outside the ultrasonic mask 1000, for example, on a lower surface of the second base layer 520.

In addition, referring to FIG. 14, the mask 1000 may be applied to a skin care device 1 to operate. In detail, referring to FIG. 14, the skin care device 1 may include a main body 10 in which one side thereof is open and including an accommodation space 11 therein.

The main body 10 may include a material that may be light and prevent damage from external impact or contact. As an example, the main body 10 may include a plastic or ceramic material, may have improved reliability from an external environment, and may protect the mask 1000 disposed inside the accommodation space 11. In addition, the main body 10 may include a viewing part 13 formed at a position corresponding to the user's eyes. The viewing part 13 may be formed in a region corresponding to the opening 1010 of the mask 1000, and the user may secure an external view through the viewing part 13.

The ultrasonic mask 1000 may be disposed in the accommodation space 11 of the main body 10. The ultrasonic mask 1000 may be disposed between the main body 10 and the user's skin. In detail, the second base layer 520 of the ultrasonic mask 1000 may be disposed to face the accommodation space 11 of the main body 10, and the first base layer 510 of the ultrasonic mask 1000 may be disposed to face the user's skin.

The ultrasonic mask 1000 may be coupled to the main body 10. For example, the ultrasonic mask 1000 may be fixed to a set position in the accommodation space 11 by a fastening member (not shown) and may have a structure that is detachable from the main body 10.

The ultrasonic mask 1000 may receive power through the power supply unit (not shown) disposed outside the mask 1000. Alternatively, the ultrasonic mask 1000 may be connected to the main body 10 to receive power through the power supply unit (not shown) disposed on the main body 10.

The ultrasonic mask 1000 may further include a buffer member (not shown) disposed on the lower surface of the second base layer 520. The buffer member may be in direct contact with the second base layer 520 and may be disposed facing the accommodation space 11 of the main body 10. That is, a deformable member may be disposed between the main body 10 and the second base layer 520 of the mask 1000.

The deformable member may include a material of which shape is changed by external pressure. For example, the deformable member may include a material such as an air gap or a sponge, but the embodiment is not limited thereto, and may include various materials of which shape is changed by external pressure. Accordingly, when the user puts on the skin care device 1, the deformable member may be deformed into a shape corresponding to the shape of the user's face. Therefore, the ultrasonic mask 1000 and the user's skin may be effectively close-adhered to each other.

In addition, when a plurality of users put on the skin care device 1, the deformable member is deformed to correspond to each face shape, so that the user's skin and the mask 1000 may be effectively close-adhered to each other.

The characteristics, structures, effects, and the like described in the above-described embodiments are included in at least one embodiment of the present invention, but are not limited to only one embodiment. Furthermore, the characteristic, structure, and effect illustrated in each embodiment may be combined or modified for other embodiments by a person skilled in the art. Thus, it should be construed that the contents related to such combination and modification are included in the scope of the present invention.

In addition, the above description has been focused on the embodiments, but it is merely illustrative and does not limit the present invention. Those skilled in the art to which the embodiments pertain may appreciate that various modifications and applications not illustrated above are possible without departing from the essential features of the embodiment. For example, each component particularly represented in the embodiments may be modified and realized. In addition, it should be construed that differences related to such a modification and an application are included in the scope of the present invention defined in the appended claims.

The invention claimed is:

1. An ultrasonic mask comprising:
a first substrate;
a first wire disposed on an upper surface of the first substrate;
a first electrode connected to the first wire and disposed on the first wire;
a piezoelectric member disposed on the first electrode;
a second electrode disposed on the piezoelectric member;
a second wire connected to the second electrode and disposed on the second electrode;
a second substrate disposed on the second wire;
a first base layer on the second substrate;
a second base layer under the first substrate;
a plurality of spacers disposed on the first base layer;
wherein the first wire and the second wire have a curvature of 5R to 15R,
wherein the piezoelectric member generates an ultrasonic wave having a frequency band of 20 kHz to 1 MHz,
wherein the piezoelectric member includes a plurality of piezoelectric elements spaced apart from each other,
wherein the plurality of piezoelectric elements are spaced apart from each other at different distances,
wherein a distance between the piezoelectric elements disposed in a first region having a first curvature is smaller than a distance between the piezoelectric elements disposed in a second region having a second curvature smaller than the first curvature,
wherein the plurality of spacers are disposed in a region of an upper surface of the first base layer that does not overlap the plurality of piezoelectric elements in a vertical direction and protrude away from each of the first substrate and the second substrate, and
wherein the plurality of spacers include:
a plurality of first spacers extending in a first horizontal direction and spaced apart from each other in a second horizontal direction perpendicular to the first horizontal direction; and
a plurality of second spacers extending in the second horizontal direction, spaced apart from each other in the first horizontal direction, and connected to the plurality of first spacers.

2. The ultrasonic mask of claim 1, wherein an elongation of the first wire and the second wire is 10% to 50%, and
wherein the elongation is a ratio of a difference between a first length and a second length, which is a maximum tensile length of each of the first and second wires, to the first length before each of the first and second wires is tensioned.

3. The ultrasonic mask of claim 1, wherein
the second base layer reflects the ultrasonic wave in a direction of the first base layer, and
a thickness of the second base layer is equal to or less than a thickness of the first base layer.

4. The ultrasonic mask of claim 1, further comprising:
a first adhesive layer disposed between the first electrode and the first wire; and
a second adhesive layer disposed between the second electrode and the second wire,
wherein
when a region where the first adhesive layer and one surface of the first electrode overlap is defined as a first overlapping region,
a region where the second adhesive layer and the other surface of the second electrode overlap is defined as a second overlapping region, and
overlapping areas of the first overlapping region and the second overlapping region are 20% or more of the entire area of the first electrode or the second electrode.

5. The ultrasonic mask of claim 4, wherein a difference between the overlapping areas of the first overlapping region and the second overlapping region is 5% to 10%.

6. The ultrasonic mask of claim 1, further comprising:
an indicator disposed on the second substrate.

7. The ultrasonic mask of claim 1, wherein a thickness of the first substrate and a thickness of the second substrate are 0.5 μm to 5 μm.

8. The ultrasonic mask of claim 4, wherein a thickness of the first adhesive layer is greater than a thickness of the second adhesive layer.

9. The ultrasonic mask of claim 1, wherein a line width of the first wire and a line width of the second wire are 50 μm to 500 μm.

10. The ultrasonic mask of claim 9, wherein a thickness of the first wire and a thickness of the second wire are equal to or less than $\frac{1}{10}$ of the line width of the first wire and the line width of the second wire.

11. The ultrasonic mask of claim 3, wherein
the first base layer includes silicon (Si), and
the thickness of the first base layer is 300 μm to 1 mm.

12. The ultrasonic mask of claim 3, wherein the second base layer includes a groove formed in a region corresponding to the piezoelectric member.

13. A skin care device comprising:
a main body in which one side thereof is an open region and an accommodation space is formed inside the open region; and
the mask of claim 3 is disposed in the open region and connected to the main body.

14. The skin care device of claim 13, further comprising a buffer member disposed on a lower surface of the second base layer.

15. The skin care device of claim 13, wherein an elongation of the first wire and the second wire is 10% to 50%.

* * * * *